United States Patent [19]

Carrillo

[11] Patent Number: 4,478,821

[45] Date of Patent: Oct. 23, 1984

[54] INHIBITION OF BODY ODOR

[75] Inventor: Angel L. Carrillo, Wellesley, Mass.

[73] Assignee: The Gillette Company, Boston, Mass.

[21] Appl. No.: 342,860

[22] Filed: Jan. 26, 1982

[51] Int. Cl.$^3$ .......................... A61K 7/32; A61K 9/12
[52] U.S. Cl. ................................ 424/47; 424/DIG. 5; 424/65; 424/326; 424/358; 424/365
[58] Field of Search .............. 424/65, 326, 47, DIG. 5

[56] References Cited

U.S. PATENT DOCUMENTS

| | | | |
|---|---|---|---|
| 3,468,898 | 9/1969 | Cutler et al. ......................... | 260/301 |
| 3,855,140 | 12/1974 | Billany et al. ........................ | 252/106 |
| 4,226,889 | 10/1980 | Yuhas .................................. | 424/65 X |
| 4,271,190 | 6/1981 | Bertelmann et al. ................ | 424/326 |
| 4,278,658 | 7/1981 | Hooper et al. ......................... | 424/65 |
| 4,279,911 | 7/1981 | Martin-Smith et al. ........ | 424/326 X |

FOREIGN PATENT DOCUMENTS

| | | | |
|---|---|---|---|
| 80755 | 3/1956 | Denmark ........................... | 424/326 |
| 2263130 | 6/1973 | Fed. Rep. of Germany ...... | 424/326 |
| 2301829 | 7/1973 | Fed. Rep. of Germany ........ | 424/65 |
| 1159174 | 6/1958 | France ................................ | 424/326 |
| 4427835 | 11/1969 | Japan .................................. | 424/326 |
| 702268 | 1/1954 | United Kingdom ................ | 424/326 |
| 1152243 | 5/1969 | United Kingdom ................ | 424/326 |
| 1407258 | 9/1975 | United Kingdom ................ | 424/326 |
| 1434040 | 4/1976 | United Kingdom ................ | 424/326 |
| 1464005 | 2/1977 | United Kingdom ................ | 424/326 |
| 1556632 | 11/1979 | United Kingdom ................ | 424/326 |
| 2074444 | 11/1981 | United Kingdom ................. | 424/70 |

OTHER PUBLICATIONS

Ash, A Formulary of Cosmetic Preparations, 1977, pp. 1 to 7.

Dravnieks, et als, "Influence of an Antibacterial Soap on Various Effluents from Axillae", *J. Soc. Cosmetics Chem.*, 19, 611–626 (1968).

Cowen, "Relative Merits of 'In Use' and Laboratory Methods for the Evaluation of Antimicrobial Products", *J. Soc. Cosmetics Chem.*, 25, 307–323 (1974).

*Primary Examiner*—Dale R. Ore
*Attorney, Agent, or Firm*—Mandel E. Slater

[57] ABSTRACT

Inhibition of body odor is obtained by applying polyhexamethylene biguanide hydrochloride to the skin in a dermatologically acceptable carrier.

4 Claims, No Drawings

INHIBITION OF BODY ODOR

BACKGROUND OF THE INVENTION

1. Field of the Invention

This invention relates to inhibition of body odor, and more particularly to a method involving topical application of a deodorant-active material for bringing about such inhibition.

2. Description of the Prior Art

As is well known, the mechanism of formation of the most common type of body odor is based upon the action of microorganisms on apocrine sweat. As a consequence of this mechanism there are in wide commercial use today in the over-the-counter toiletries and cosmetics category two types of products that inhibit body odor, deodorants and antiperspirants, the latter group also occasionally referred to as antiperspirant-/deodorants. The former group is meant to include products containing an active material which inhibits the growth of microorganisms present on the skin and thereby prevents their action on sweat to produce odoriferous substances. The latter group is meant to include products which contain materials that inhibit sweating in the first place. For various reasons, such as aesthetic preference, sensitivity to certain astringent antiperspirants salts, etc., individual consumers who wish to use a product in this board category may prefer one or the other type. The present invention has to do with improvements in deodorants.

Although a number of deodorant-active materials have been used in the past in the formulation of personal deodorant products, for many years the most widely used such material was hexachlorophene, possibly the most efficacious topical deodorant then available. However, as is well known, about a decade ago a previously unrecognized toxicity problem with hexachlorophene was identified, and non-prescription use of this material had to be severely restricted. Fortunately other deodorant-active materials were available, among which mention may be made of benzethonium chloride, triclosan, etc., and industry had adapted by substituting these and others in various products which formerly used hexachlorophene. However it was perceived by many that the substitute materials did not necessarily provide parity performance. Consequently the search for safe and effective materials with improved deodorant activity has continued.

Since, as has been mentioned previously, the deodorant-active materials under consideration act by inhibiting the growth of microorganisms on the skin, it would initially appear that any good antimicrobial should be effective as a deodorant. In fact, however, no correlation has been observed, i.e., while known deodorants also have good antimicrobial properties, it does not follow that good antimicrobials will be effective as deodorants. For example the following materials, all antimicrobials, were tested for deodorant activity according to the test procedures reported hereinafter for the present invention, and no improvement over currently available materials was observed and in some cases no deodorant activity at all: hydrogen peroxide, chlorhexidine, triacetin, and 3-(trimethoxysilyl)-propyloctadecyldimethyl ammonium chloride (Dow-Corning, Q9-5700). The unpredictability of deodorant activity is especially to be noted in the case of chlorhexidine, which contains biguanide function similar to the improved deodorant of the present invention. Other workers have also noted this poor correlation between antimicrobial activity and deodorant activity; see, for example, Dravnieks, Krotoszynski, Lieb, and Jungermann, "Influence of an Antibacterial Soap on Various Effluents from Axillae," *J. Soc. Cosmetic Chemists,* 19, 611–626 (1968) and Cowen, "Relative Merits of 'In Use' and Laboratory Methods for the Ealuation of Antimicrobial Products," *J. Soc. Cosmetic Chemists,* 25, 307–323 (1974).

SUMMARY OF THE INVENTION

It is an object of the present invention to provide improved inhibition of body odor. With this object in view a feature of the present invention is the inhibition of body odor by applying to the skin, in a carrier which is dermatologically acceptable, an effective amount of polyhexamethylene biguanide hydrochloride. Good odor inhibition is obtained, which is seen to be as good as or superior to that obtained from the use of typical deodorant materials in wide commercial use.

For the purposes of the present invention polyhexamethylene biguanide hydrochloride is defined as the compound having the following formula:

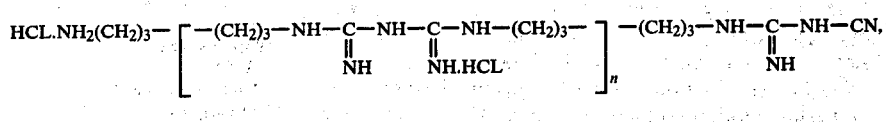

where n averages 4.5 to 6.5. Polyhexamethylene biguanide hydrochloride is commercially available from ICI Americas Inc., Wilmington, Delaware, under the name "Cosmocil CQ." Its stability, compatability, and low toxicity make it suitable for use in a wide variety of products in the cosmetics and toiletries field. For example, the deodorant benefits of utilizing polyhexamethylene biguanide hydrochloride may be realized by incorporating this material in aqueous-alcoholic solutions, lotions, creams, ointments, powders, suspensions, soaps, waxes and gels in stick form, and compositions for pressurized dispensing in the form of an aerosol, all of conventional formulation. The minimum effective concentration of polyhexamethylene biguanide hydrochloride may be determined by routine trial-and-error. At high concentrations the material can be a skin irritant, and cost considerations militate against using too much. I prefer to use from about 0.05% to about 2%. A concentration of about 0.4% of the total composition has given particularly good results; this means using 2% of the active material, which in its commerical form is suplied as a 20% aqueous solution.

TEST PROCEDURE

Materials under consideration for deodorant efficacy were evaluated in direct comparison tests on human axillae, one axilla treated with the test product and the other with a control product. In order to eliminate any side bias, about half the panel in each study received the test product on the right axilla and about half on the left. Each study involved about 50 male test panelists at the outset, usually a slightly smaller number at the conlusion due to minor attrition. The test period covered two weeks, the first a "washout" period and the second for the actual test. Panelists were instructed to abstain from the use of all deodorants, antiperspirants, and medicated products on their underarms during the entire two weeks of the study, and a non-deodorant soap was provided for bathing. During the second week panelists were instructed to avoid their underarms while bathing/showering (Sunday noon through Friday morning). The only deodorant or antiperspirant products applied during the test (second) week were the test and control products. Control odor evaluations were generally made on Monday and Tuesday of the test week, with applications of the test materials after the odor evaluations on Tuesday through Friday. Since deodorants are typically used once daily, twenty-four hour post-treatment evaluations were made on Wednesday through Friday, prior to further treatment. Odor evaluations at shorter post-application intervals are frequently made, but the 24-hour measurements are considered the most important. All 24-hour odor evaluations were followed by a supervised wash, after which the panelists' axillae were checked by an experienced odor judge for cleanliness and complete soap removal. Product application followed the wash.

Axillary odor was scored on a zero (no odor) to ten (very intense, disagreeable odor) scale by a panel of four experienced odor judges for each axilla. Judges were blinded as to treatment assignments, other judges' scoring, and previous evaluations for panelists. In order to limit each study to panelists who, without treatment, are high odor producers, any panelists whose average odor score was less than 3.0 on Monday was eliminated from the test. The odor evaluation procedure had each panelist remove all clothing to the waist, stand before each odor judge in sequence and present the right axilla first, the left axilla second. Panelists were instructed to keep arms down to sides until the judges were ready to make their evaluations.

Application consisted of about eight to ten strokes of the appropriate formulation applied by a technician to the designated axilla, the exact of number of strokes being appropriate, as determined by the technician's experience, to apply about 0.5 gram of formulation. Product applications were made by the same technician throughout the test. Each panelist was assigned his own individual test unit of each product. Product containers were weighed at the beginning and at the end of the test to verify the amount of product used.

The odor scores given by the four odor judges were averaged and subjected to statistical analysis to determine whether a particular test product or its control was more effective at reducing axillary door. Score differences were considered significant only at the 95% confidence level or higher.

EXAMPLE I

This study compared the deodorant efficacy of polyhexamethylene biguanide hydrochloride at 0.4% absolute concentration in 75/25 SD 40 alcohol/water wt/wt, with benzethonium chloride (Rohm & Haas Co., Hyamine 1622) as a 0.2% solution (typical concentration in commercially-available deodorants) in the same vehicle. The study began with 47 panelists and concluded with 43. The test procedure described above was followed with the exception that applications began on Monday, so that base line readings (no treatment) were obtained for only one day and 24-hour post-application readings for four days, Tuesday through Friday. The average odor ratings are given in the following table:

| Day | Polyhexamethylene Biguanide Hydrochloride | Benzethonium Chloride | Difference |
|---|---|---|---|
| control 1 | 4.63 | 4.80 | −0.17 |
| post-application 1 | 3.94 | 4.12 | −0.18 |
| post-app. 2 | 3.84 | 4.48 | −0.64 |
| post-app. 3 | 3.67 | 4.12 | −0.45 |
| post-app. 4 | 3.66 | 4.08 | −0.42 |

The polyhexamethylene biguanide hydrochloride performed at parity with benzethonium chloride on the first post-application day and was significantly superior throughout the last three days of the test, indicating superior deodorant efficacy of polyhexamethylene biguanide hydrochloride.

EXAMPLE II

In this study polyhexamethylene biguanide hydrochloride was again compared with benzethonium chloride, with the deodorant materials incorporated in a formulation suitable for a roll-on deodorant. The compositions were as follows:

|  | Test Product | Control |
|---|---|---|
| Magnesium aluminum silicate | 22.500 | 22.500 |
| Deionized water | 66.575 | 68.375 |
| Methylparaben | 0.200 | 0.200 |
| Propylparaben | 0.200 | 0.200 |
| EDTA | 0.025 | 0.025 |
| Polyoxyethylene (4) lauryl ether (Brij 30 - ICI Americas) | 0.500 | 0.500 |
| Glyceryl stearate PEG-100 stearate | 7.000 | 7.000 |
| Dimethicone | 1.000 | 1.000 |
| Benzethonium chloride (Hyamine 1622) | — | 0.200 |
| Polyhexamethylene biguanide Hydrochloride | 2.000 | — |
|  | 100.000% | 100.000% |

The following odor scores were obtained with 56 panelists throughout:

| Day | Polyhexamethylene Biguanide Hydrochloride | Benzethonium Chloride | Difference |
|---|---|---|---|
| control 1 | 4.62 | 4.58 | 0.04 |
| control 2 | 4.42 | 4.46 | −0.04 |
| post-app. 1 | 4.40 | 4.63 | −0.23 |
| post-app. 2 | 4.29 | 4.69 | −0.40 |
| post-app. 3 | 4.09 | 4.55 | −0.46 |

The polyhexamethylene biguanide hydrochloride was significantly superior to benzethonium chloride on the second and third post-application days.

EXAMPLE III

This study utilized as a formulation base a representative commercial sodium stearate-type deodorant stick, such as is well known in the art, but without the fragrance. The control product consisted of SD alcohol 40, 76.43%; water, 11.51% sodium stearate, 7.0%; propylene glycol, 4.0% fragrance, 1.0% and triclosan (Ciba-Geigy Corp., Irgasan DP-300), 0.06%. In the test product the triclosan was replaced by 2% polyhexamethylene biguanide hydrochloride, adjusting the concentration of the water only. The test panel varied between 44 and 47 subjects. Odor scores are as follows:

| Day | Polyhexamethylene Biguanide Hydrochloride | Triclosan | Difference |
| --- | --- | --- | --- |
| control 1 | 4.61 | 4.55 | 0.06 |
| control 2 | 4.54 | 4.81 | −0.27 |
| post-app. 1 | 3.70 | 4.02 | −0.32 |
| post-app. 2 | 3.78 | 4.40 | −0.62 |
| post-app. 3 | 3.38 | 4.06 | −0.68 |

Polyhexamethylene biguanide hydrochloride was significantly superior to triclosan as a deodorant starting with the second post-application day of the study, again showering superior efficacy in regular daily use.

I claim:
1. A method of inhibiting body odor by applying to the skin an effective deodorant amount of polyhexamethylene biguanide hydrochloride, in a dermatologically acceptable carrier.
2. The method of claim 1, in which said carrier is selected from the group consisting of aqueous-alcoholic solutions, lotions, creams, ointments, powders, suspensions, soaps, waxes in stick form gels in stick form, and aerosols.
3. The method of claim 1, in which the polyhexamethylene biguanide hydrochloride is present in an amount of from about 0.05% to about 2%.
4. The method of claim 3, in which the polyhexamethylene biguanide hydrochloride comprises about 0.4% of the total composition.

* * * * *